(12) United States Patent
Wendorf

(10) Patent No.: US 7,683,235 B2
(45) Date of Patent: Mar. 23, 2010

(54) ADHESIVE BANDAGE CARRIER AND BANDAGE DISPENSING ASSEMBLY THEREFOR

(76) Inventor: John W. Wendorf, N3244 Pine Rd., Cascade, WI (US) 53011

( * ) Notice: Subject to any disclaimer, the term of this patent is extended or adjusted under 35 U.S.C. 154(b) by 912 days.

(21) Appl. No.: 11/351,639

(22) Filed: Feb. 10, 2006

(65) Prior Publication Data

US 2007/0191753 A1   Aug. 16, 2007

(51) Int. Cl.
  *A61F 13/00* (2006.01)
  *G07F 11/66* (2006.01)
  *G07F 11/68* (2006.01)
(52) U.S. Cl. .............................. 602/57; 602/41; 602/42; 206/441; 221/25; 221/73
(58) Field of Classification Search ................ 206/440, 206/441; 128/888.889; 602/41–59; 221/225, 221/40, 46, 25, 73, 226, 222
See application file for complete search history.

(56) References Cited

U.S. PATENT DOCUMENTS 3,194,717 A * 7/1965 Donald ........................ 428/56

7,077,289 B2 * 7/2006 Ross ........................... 221/225

* cited by examiner

*Primary Examiner*—Kim M Lewis
(74) *Attorney, Agent, or Firm*—Joseph S. Heino; Patrick M. Bergin

(57) ABSTRACT

A dispenser assembly includes a housing having a face and an aperture that allows adhesive bandage carrier to pass through it. The adhesive bandage carrier comprises a longitudinally-extending carrier strip having a plurality of longitudinally-disposed adhesive bandages removably secured to an underlying carrier strip. The bandages are located at predetermined and equally-spaced intervals along the strip. At the same intervals, the strip includes a plurality of apertures. A first edge of the bandage overlays a portion of an aperture such that the first edge can be easily grasped when the bandage is dispensed. The dispenser assembly also includes a number of rotational elements that serve as either "feed" mechanisms for delivering a roll of adhesive bandage carrier from within the container or "take-up" mechanisms for accumulating protective material that overlays the bandage carrier. Different embodiments of the assembly afford mechanical and electrical actuation of the dispensing assembly.

26 Claims, 7 Drawing Sheets

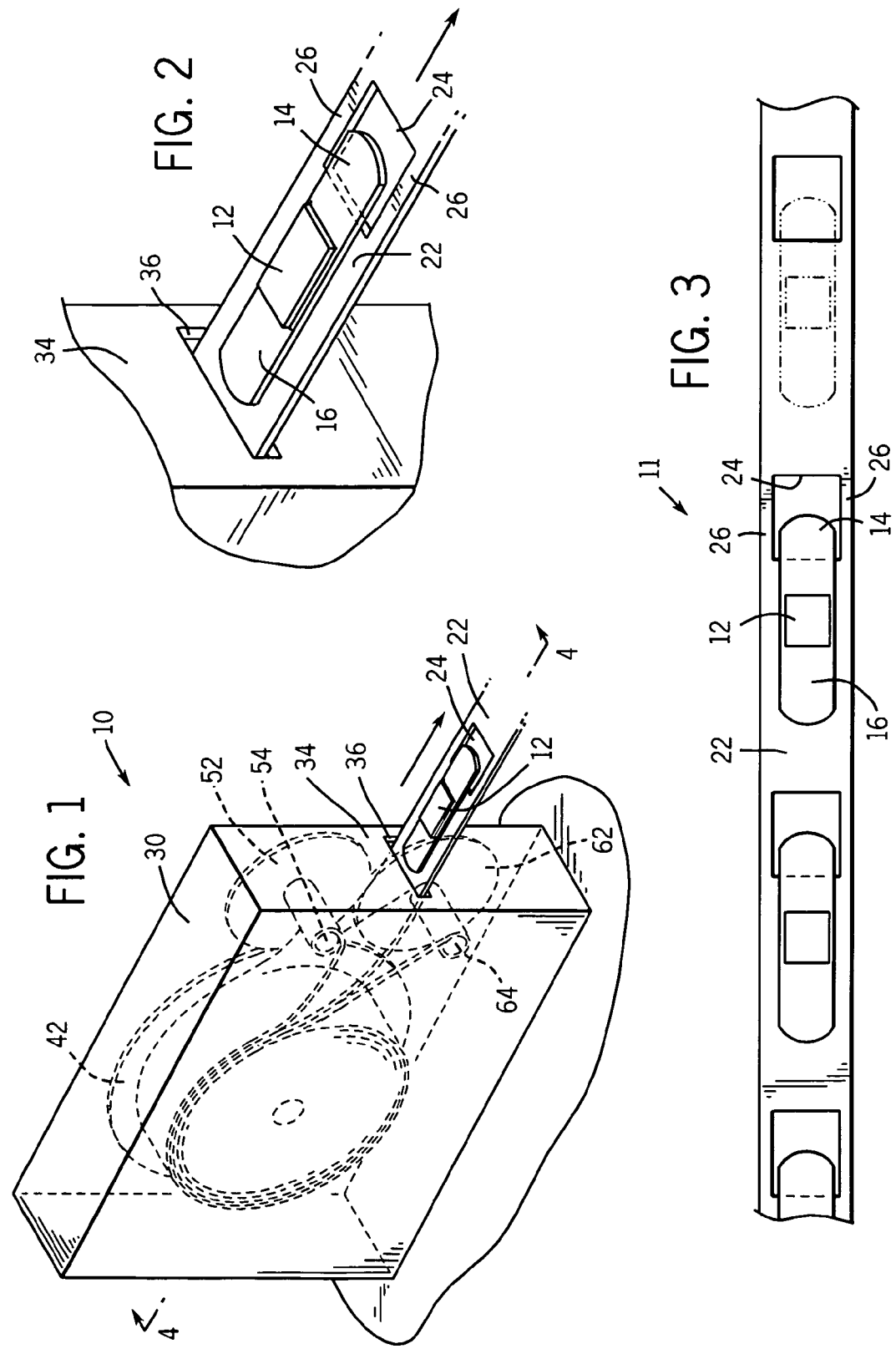

ADHESIVE BANDAGE CARRIER AND BANDAGE DISPENSING ASSEMBLY THEREFOR

FIELD OF THE INVENTION

The present invention relates generally to adhesive tapes, adhesive bandages, and to assemblies for dispensing such tapes and bandages. More specifically, it relates to an adhesive bandage carrier that has an aperture defined within the carrier such that a leading edge of the bandage can be easily grasped by the user and the bandage removed from the carrier. It also relates to an assembly for dispensing adhesive bandages from the carrier.

BACKGROUND OF THE INVENTION

In the area of adhesive bandages that are used to cover wounds and the like, it is known that application of the bandage begins with removing the bandage from a sterile envelope of some sort. Removal of the bandage typically requires the user to grasp the sterile envelope in one hand and then tear the envelope open with the other hand, clearly a two-handed operation. Once removed from the envelope, the bandage typically includes other coverings for the adhesive portion of the bandage, again requiring that the bandage be held in one hand and the adhesive coverings be removed with the other hand. This is another two-handed operation. After these steps have been taken, the user can then place the bandage over the wound, such placement being a single-hand operation in most instances.

In the experience of this inventor, time is wasted while searching this envelope or packaging for the proper end to open. Once done, the user must spend time peeling away the adhesive coverings, creating wasted and loose material at each step in the process. In the medical setting, the old method described above wastes valuable time and an extraordinary amount of wasted paper and other material. In emergency settings, this is clearly unacceptable. In addition to wasted time and material, extra handling of the bandage increases the risk of infection for the patient through extra contact with the bandage and prolonged wound exposure.

What is needed is a faster, cleaner and more economical way to dispense adhesive bandages of present manufacture. What is also needed is such a way to dispense such bandages that can be used in an institutional setting, in a home setting, or in any other setting that would require care pertaining to the application for an adhesive bandage. Accordingly, such bandage dispensing would be useful in medical offices, hospitals, clinics, emergency vehicles, workplaces, military arenas, schools and homes, basically anywhere that adhesive bandages are used. What is also needed is such a style of device to serve this purpose that accommodates a person of any age or disability and allowing for single-handed receipt of an adhesive bandage and in a way that the bandage is received in a ready-to-be-applied manner, thus avoiding unnecessary steps in the application of the adhesive bandage. What is also needed is such a style of device that is available to accommodate different size bandages and to also allow for refilling of the dispensing unit when bandages are depleted. What is also needed is such a dispensing assembly that is reasonable in cost so that the device is economical to use in all settings. What is also needed is such a dispensing assembly that can be provided as a mechanically-operated unit or as an electrically-operated unit. What is also needed is such a dispensing assembly that can actuate the dispensing of the bandage by mechanical means or by electronic or other sensing means. What is also needed is such a dispensing assembly that is convenient to store in the home or elsewhere.

SUMMARY OF THE INVENTION

Accordingly, a primary objective of the device of the present invention is to provide an improved adhesive bandage carrier and an assembly for dispensing such adhesive bandage carrier that results in a faster, cleaner and more economical way to dispense adhesive bandages of present manufacture. It is another object of the present invention to provide such a carrier and dispenser assembly such that the carrier and assembly can be used in an institutional setting, in a home setting, or in any other setting that would require care pertaining to the application for an adhesive bandage. It is still another object of the present invention to provide such a carrier and dispensing assembly that can be used by persons of any age or disability and can allow for single-handed receipt of an adhesive bandage in such a way that the bandage is received in a ready-to-be-applied manner. It is yet another object of the present invention to provide such a carrier and dispensing assembly that is available to accommodate different size bandages and that also allows for refilling of the dispensing assembly when bandages are depleted. It is still another object of the present invention to provide such a carrier and dispensing assembly that is reasonable in cost so that the device is economical for use in all settings. It is still another object of the present invention to provide such a carrier and dispensing assembly that can be fabricated as a mechanically-operated unit or as an electrically-operated unit, and that can be fabricated to actuate the dispensing of the bandage by mechanical means or by electronic or other sensing means. It is yet another object of the present invention to provide such a carrier and dispensing assembly that is convenient for use and storage in the home or elsewhere.

The present invention has accomplish these objectives. In general, a dispenser assembly is provided and is used to dispense an adhesive bandage carrier. The dispenser assembly includes a dispenser housing or enclosure that defines an interior area. The dispenser enclosure includes a face having an aperture defined in it. The opening allows the adhesive bandage carrier to pass through it. The adhesive bandage carrier comprises a longitudinally-extending carrier strip. A plurality of longitudinally-disposed adhesive bandages are removably secured to an underlying carrier strip. The bandages are located at pre-determined and equally-spaced intervals along the strip. At substantially the same pre-determined intervals, the strip includes a plurality of apertures. To either side of the aperture is a relatively thin portion of carrier strip material. A leading edge or, alternatively, a trailing edge of the bandage overlays a portion of the carrier strip aperture. Thus, the leading edge or the trailing edge of the bandage can be easily grasped by the user when the bandage is dispensed, together with the carrier strip, from the dispenser. The internal area of the dispenser assembly includes, in the first embodiment, a first rotational means, a second rotational means, and third rotational means. The first rotational means is intended to be a "feed" means for delivering a roll of adhesive bandage carrier from within the container to its exterior. The second and third rotational means are each intended to be a "take-up" means for other material that overlays the adhesive bandage carrier, such take-up to be accomplished within the container. Other embodiments of the assembly of the present invention are provided including other mechanical and/or electrical actuation of the dispensing process provided by the present invention.

The foregoing and other features of the apparatus and assembly of the present invention will be apparent from the detailed description that follows.

BRIEF DESCRIPTION OF THE DRAWINGS

FIG. 1 is a top, front and left side perspective view of a first embodiment of an assembly that is used to dispense adhesive bandages from a carrier in accordance with the present invention.

FIG. 2 is an enlarged top, front and left side view of the bandage and carrier shown exiting the assembly illustrated in FIG. 1.

FIG. 3 is a top plan view of the adhesive bandage carrier that is constructed in accordance with the present invention.

DETAILED DESCRIPTION

Figure 4:
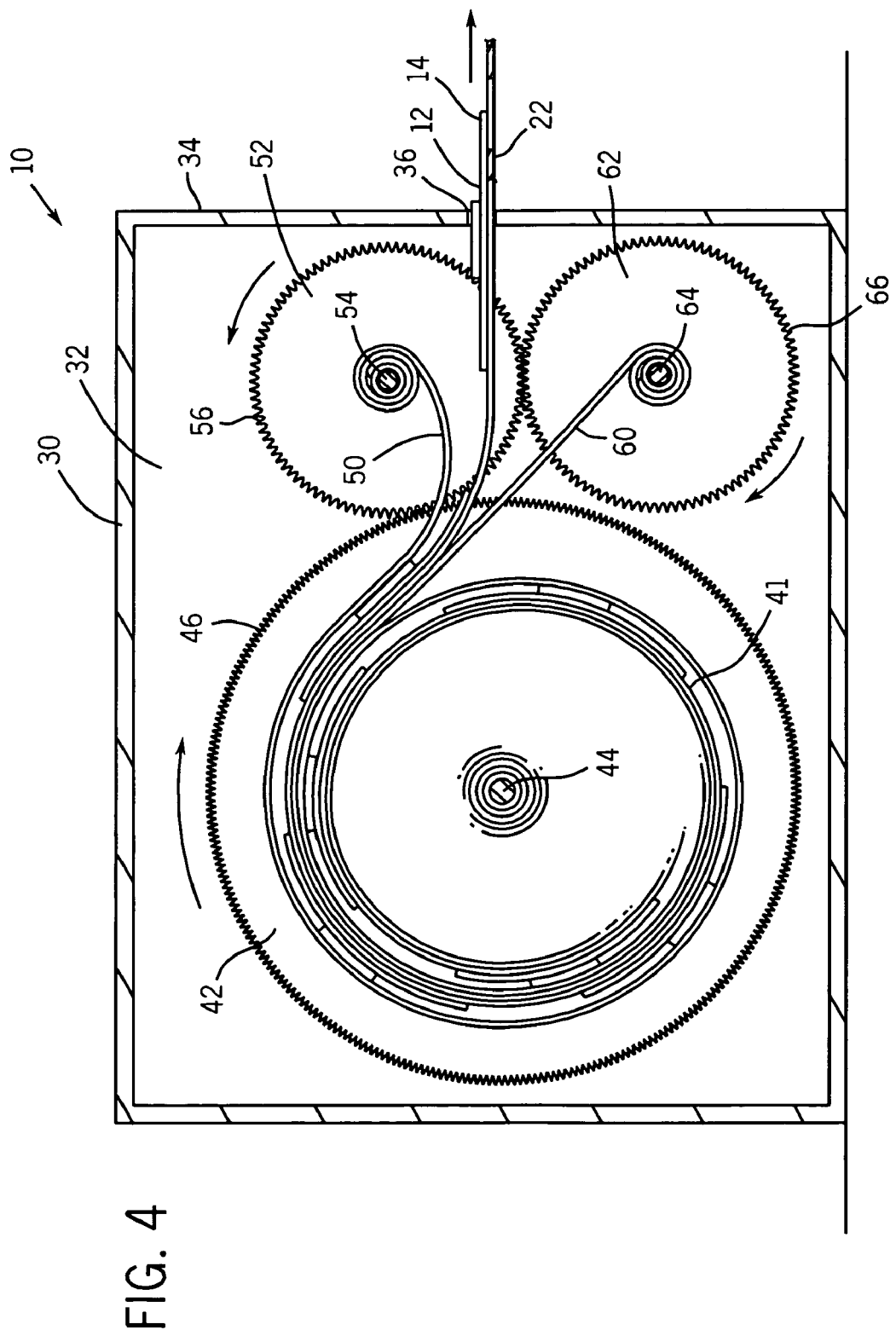
FIG. 4 is an enlarged side elevational and cross-sectioned view of the bandage dispensing assembly shown in FIG. 1 and taken along line 4-4 of FIG. 1.
Figure 5:
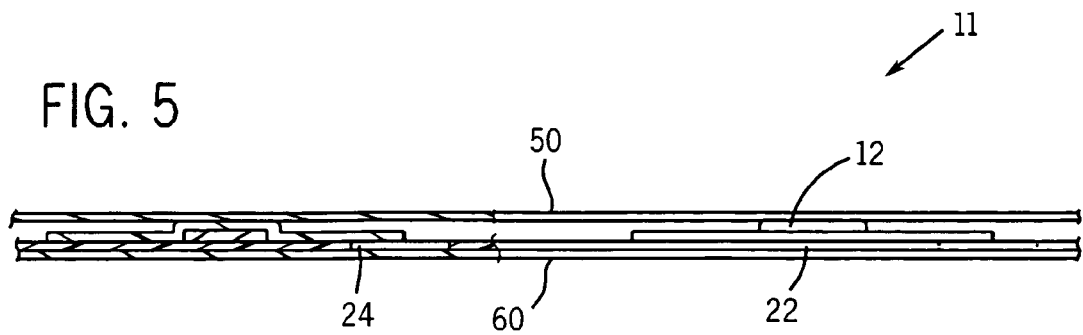
FIG. 5 is an enlarged side elevational and partially cross-sectioned view of the bandage carrier illustrated in FIG. 3.

Referring now to the drawings in detail wherein like numbers represent like elements throughout, FIG. 1 illustrates the first preferred embodiment of a dispenser assembly, generally identified 10, that is used to dispense an adhesive bandage carrier, generally identified 11, in accordance with the present invention. In general, the dispenser assembly 10 includes a dispenser housing or enclosure 30 that defines an interior area 32. Also see FIG. 4. The dispenser enclosure 30 includes at least one face 34 having an aperture 36 defined within it. See FIG. 2. As shown, the aperture 36 that is defined within the face 34 of the container 30 is a generally elongated and rectangular opening. The reason for this shape of aperture 36 is that the aperture 36 must be able to allow the adhesive bandage carrier 11, as shown in FIG. 3, to pass through it. It is to be understood that the enclosure may be fabricated from any number of materials such as cardboard, plastic or the like. It can also be fabricated from foldable paperboard stock where at least two sides include flaps that are insertable within openings such that the container 30 is readily assembled, manually or mechanically. The container 30 may also assume different geometries without deviating from the scope of the present invention. That is, the container 30 is not intended to be limited to the rectangular box-like structure illustrated in the figures shown. Other shapes could be used without adversely affecting the overall functionality of the assembly 10. Regardless of shape, the container 30 should also be fabricated such that the interior area 32 of it is accessible for replenishing the supply of adhesive bandage carrier 11 that is dispensed by the assembly 10 of the present invention. Thus, the assembly 10 can be refillable.

Figure 7:
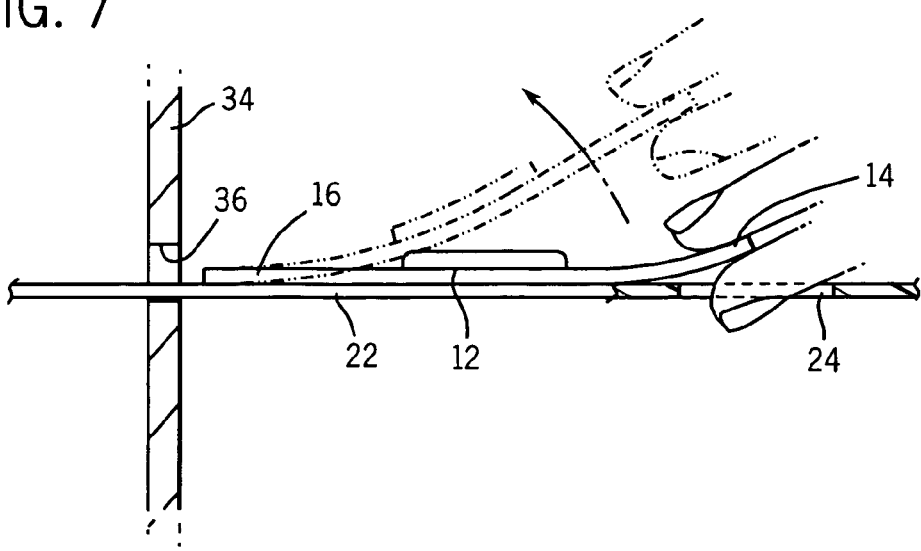
FIG. 7 illustrates how the user would lift an adhesive bandage away from the carrier strip as the bandage and carrier exit the dispenser assembly as shown in FIG. 6.

Referring specifically to FIG. 3, it will be seen that the adhesive bandage carrier 11 comprises a longitudinally-extending carrier strip 22, it being noted that only a segment of the total strip 22 is shown. A plurality of longitudinally-disposed adhesive bandages 12 are removably secured to an underlying carrier strip 22. In the preferred embodiment, the carrier strip 22 is made of a material that is resistant to complete adhesion of the bandage 12 to it, thereby allowing the bandage 12 to be easily drawn away from the carrier strip 22 for placement of the bandage 12 onto another surface, such as the skin of a person. The bandages 12 are located at pre-determined and equally-spaced intervals along the strip 22. At substantially the same pre-determined intervals, the strip 22 includes a plurality of apertures 24 that are defined within the strip 22. To either side of the aperture 24 is a relatively thin portion 26 of carrier strip 22 material. In this fashion, the carrier strip 22 is longitudinally continuous with the aperture side portions 26 being of such dimension that the carrier strip 22 can be severed or torn at the side portions 26 after a bandage 12 has been removed from the carrier strip 22. It is to be understood, however, that the shape of the aperture 24 may be different than is shown without deviating from the scope of this invention. As shown in FIG. 3, the bandage 12 is a common rectangular-shaped adhesive bandage of current manufacture that includes a first adhesive edge portion 14 and a second adhesive edge 16. Here again, the shape and size of the bandage 12 may be different than is shown without deviating from the scope of this invention. The first edge adhesive portion 14 of the bandage 12 extends and overlays a portion of the carrier strip aperture 24. In this fashion, the first edge 14 of the bandage 12 can be easily grasped by the user when the bandage 12 is dispensed, together with the carrier strip 22, from the dispenser 30 as is more clearly shown in FIG. 7. The bandage 12 can then be easily lifted upwardly and away from the carrier strip 22 as is also shown in phantom view in FIG. 7. Once removed, the bandage 12 can be applied as desired or required by the user.

Figure 12:
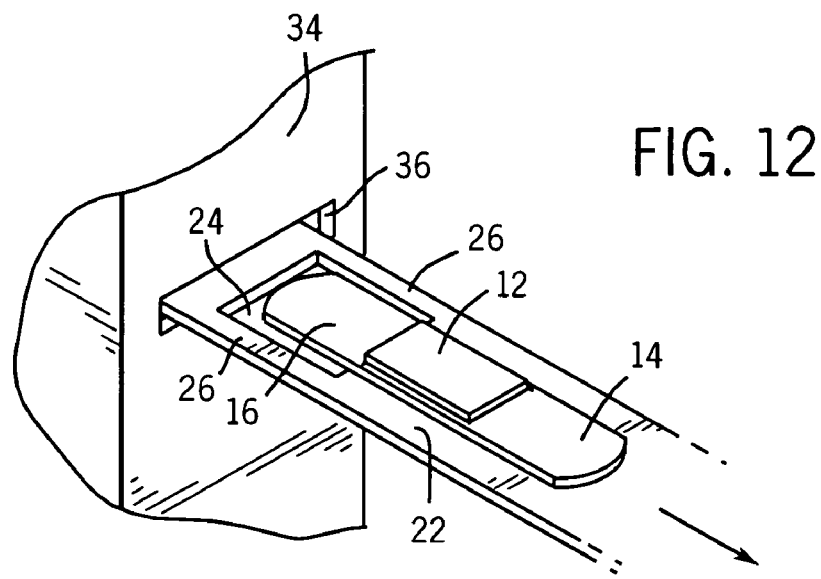
FIG. 12 is a view similar to FIG. 2, but showing the bandage and carrier exiting the assembly where the carrier aperture is at a trailing edge of the bandage.

As alluded to previously, the first adhesive edge portion 14 of the bandage 12 will be considered as the "leading" edge when the carrier strip 22 is dispensed from the dispenser 30 as is shown in FIG. 2. Alternatively, the first adhesive edge portion 14 of the bandage 12 will be considered as the "trailing" edge when the carrier strip 22 is dispensed from the dispenser 30 as is shown in FIG. 12. Pre-wrapping of the carrier 11 will determine whether the first adhesive edge portion 14 is presented as the leading edge or as the trailing edge of the bandage 12. It is to be understood that the carrier 11 of the present invention is not limited to either presentation and both are covered by the claims herein.

Referring again to FIGS. 1 and 4 in particular, it will be seen that the internal area 32 of the dispenser assembly 10 includes, in the first embodiment, a first rotational means in the form of a first gear 42, a second rotational means in the form of a second gear 52, and third rotational means in the form of a third gear 62. It is to be understood that this configuration could be varied and the rotational means and gear drive arrangement could be configured differently without deviating from the scope of this invention. The first rotational means is intended to be a "feed" means for delivering a roll 41 of adhesive bandage carrier 11 from within the container 30 to its outside. The second and third rotational means are each intended to be a "take-up" means for other material that overlays the adhesive bandage carrier 11, such take-up to be accomplished within the container 30.

In the first preferred embodiment of the assembly 10, it is to be understood that the first rotational means 42, the second rotational means 52, and the third rotational means 62 include engagement means such that each rotational means 42, 52, 62 is engagable with at least one other rotational means 42, 52, 62 such that movement of one rotational means effects or results in the rotation of one or more of the other rotational means. In the preferred embodiment, gear teeth are used for this purpose, but the invention is not so limited. Any structure that effects coordinated rotation of the rotational means is within the scope of the present invention.

Returning again to FIG. 1, it will be seen, in phantom view, just how the first gear 42 is used as the internal "source" carrier or "feeder" for the bandage carrier 11 where the bandage carrier 11 is pre-wrapped about a centrally-disposed spool or pin 44. Thus, when the first gear 42 is rotated in the clockwise direction as viewed in FIG. 4, the bandage carrier 11 unwinds from the pin 44 and gear 42 arrangement. This rotation is initiated by the user placing tension on that part of the carrier 11 that extends outwardly of the container 30. In the preferred embodiment, the pin 44 and gear 42 would be a unitary structure, but such is not a limitation of the present invention. It should be noted here that the important functionality in this embodiment is that the pre-wound roll 41 of bandage carrier 11 rotates with the gear 42 as the gear 42 rotates when the user pulls on that portion of the carrier 11 that is external to the container 30 at the slotted aperture 36.

The first gear 42 has a plurality of teeth 46 defined about it perimeter. As shown in this particular embodiment, the teeth 46 of the first gear 42 mesh with the gear teeth 56 of the second gear 52, the second gear 52 also including a centrally-disposed spool or pin 54. In turn, the teeth 56 of the second gear 52 are used to mesh with gear teeth 66 of a third gear 62, the second gear 62 also including a centrally-disposed spool or pin 64. As alluded to earlier, the second gear 52 and pin 54 are each used in combination as a "take-up" means or mechanism that is provided to gather remnant material of a first protective covering 50 that overlays the bandage carrier 11 from the top. Similarly, the third gear 62 is provided as a "take-up" means or mechanism to gather remnant material of a second protective covering 60 that overlays the bandage carrier 11 from the bottom. It is to be understood that the protective coverings 50, 60 are also longitudinally-extending members that are preferably sealed at the longitudinal edges of the coverings 50, 60 to maintain the sterile environment in which the carrier 11 is contained. The coverings 50, 60 are sealed sufficiently to encapsulate the carrier 11 but not so securely sealed that the edges cannot be separated to allow proper functioning of the dispenser assembly 10. That is, the coverings 50, 60 should be capable of being separated from one another when the dispenser assembly 10 is used as intended.

Figure 14:
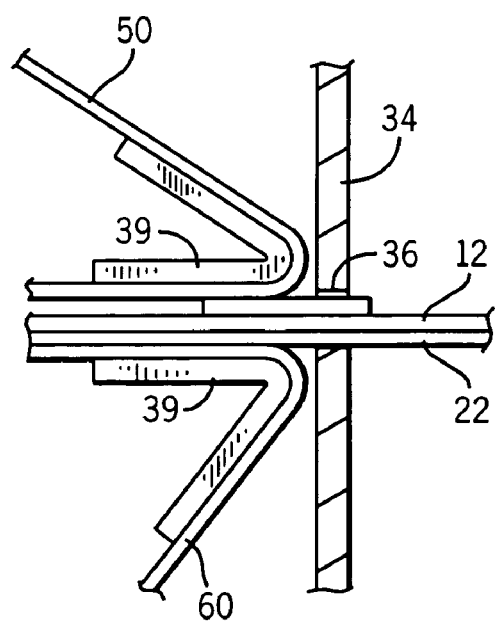
FIG. 14 is an enlarged and partially cross-sectioned view of an alternative embodiment of outlet guide means in the form of bent planar members.
Figure 13:
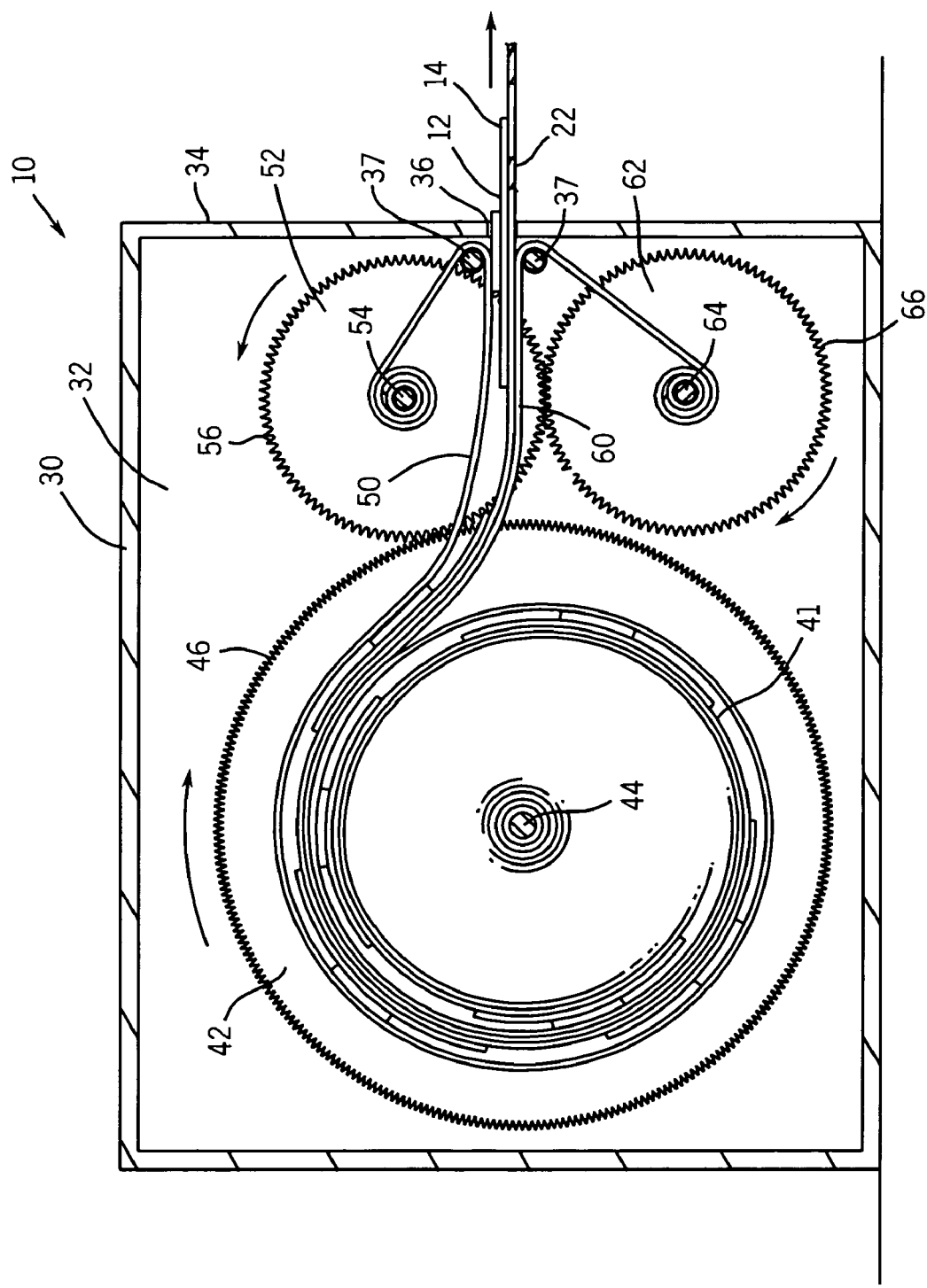
FIG. 13 is a view similar to FIG. 1, but showing guide means in the form of rollers disposed at the dispenser outlet.

The dispenser may also be configured to include additional guide means such that the protective coverings 50, 60 are removed from the carrier 22 at a point that is much closer to the slotted aperture 36. See FIGS. 13 and 14. The guide means can take the form of the rollers 37 or bent planar members 39.

Figure 6:
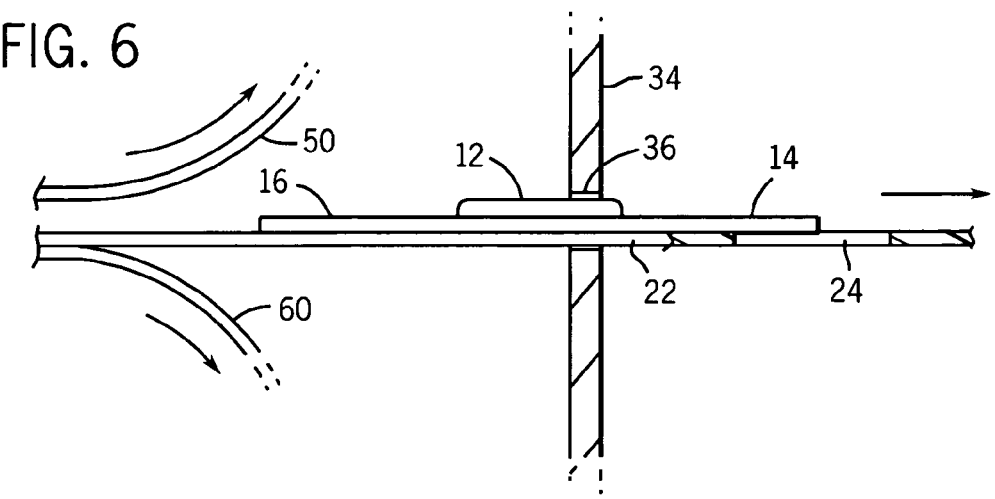
FIG. 6 is a further enlarged side elevational view showing the adhesive bandage carrier as it exits from the dispenser assembly illustrated in FIG. 1.

In application, and as a user pulls a leading edge of the bandage carrier 11 from the assembly 10, the applied tension causes the first gear 42 to be rotated in a clockwise direction, which moves the second gear 52 in a counterclockwise direction, which in turn moves the third gear 62 in a clockwise direction. In this way, bandage carrier 11 is unwound and drawn away from the first gear 42 and pin 44 and the protective covering material 50, 60 is taken up by the second gear 52 and pin 54 and the third gear 62 and pin 64, respectively. See also FIGS. 6 and 7. The user can then use one hand to grasp the first edge 14 of the bandage 12, such first edge 14 overlaying the carrier aperture 24. The carrier aperture 24 facilitates the user's ability to grasp that first edge 14. As the user continues to pull the first edge 14 of the adhesive bandage 12, the bandage 12 is pulled upwardly and away from the carrier strip 22. This action is repeated as desired or required. In the preferred embodiment, the remnant carrier strip 22 from which bandages 12 have been removed can also be disposed of by tearing the strip 22 at the thin portions 26 of carrier strip 22 material.

It is also to be noted that the container 30 could also be configured such that the feed mechanism 42 and the take-up mechanisms 52, 54, 62, 64 form part of a pre-fabricated subassembly (not shown) where replenishment of the roll 41 of carrier 11 could be accomplished by simple replacement of that complete subassembly within the container 30. Alternatively, replenishment could be accomplished simply by replacing the roll 41 and threading of the coverings 50, 60 onto the take-up mechanisms 54, 64 and the carrier 11 through the container aperture 36. Both configurations are contemplated by the carrier 11 and assembly 10 of the present invention. It is to be understood that the same roll-replacement concepts apply to the other preferred embodiments that are discussed herein.

Figure 8:
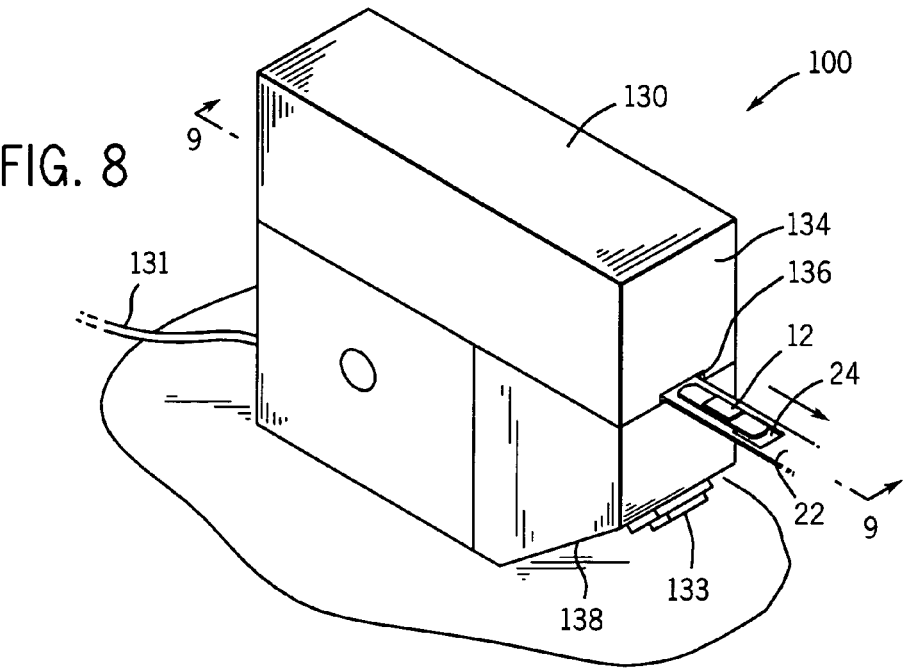
FIG. 8 is a top, front and left side perspective view of a second embodiment of an assembly that is used to dispense adhesive bandages from a carrier in accordance with the present invention.

Referring now to FIG. 8, it illustrates a second preferred embodiment of a dispenser assembly, generally identified 100, that is used to dispense bandage carrier 11 in accordance with the present invention. In general, the dispenser assembly 100 includes a dispenser enclosure 130 that defines an interior area 132. The dispenser enclosure 130 includes a face 134 having an aperture 136 defined in it. As shown, the opening 136 that is defined within the face 134 of the container 130 is also a generally elongated and rectangular opening for the reason that the opening 136 must be able to allow the bandage carrier 11 to pass through it. The container 130 of this embodiment also includes a second face 138 that has a push-button 133 disposed within it. The push-button 133 is electrically connected via a wire 135 to a motor 170. It is to be understood that the push-button 133 could be any type of electrical switch that is movable from an "off" position to an "on" position. In this way, the motor 170 is selectively actuated by means of the push-button 133 and an electrical cord 131 that is wired to and through the container 130. The precise type of push-button or switch 133, and its placement relative to the container 130, are not limitations of the present invention. It is also within the scope of the present invention that the actuation means provided by the push-button 133 could also be provided by an infrared sensor (not shown) whereby the assembly 100 could be actuated simply by the user passing his or her hand over, or in the vicinity of, the sensor to activate the motor 170. It is also within the scope of the present invention that the motor 170 be a direct current device that is driven by one or more batteries (not shown).

Figure 9:
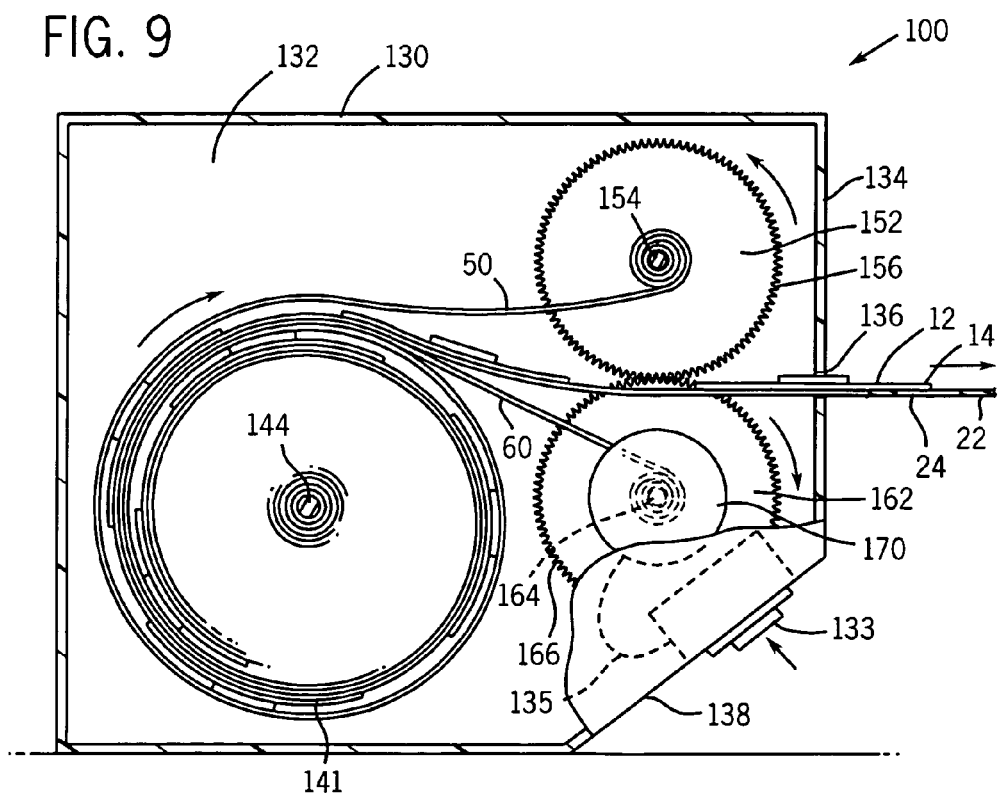
FIG. 9 is an enlarged left side elevational and cross-sectioned view of the dispenser assembly illustrated in FIG. 8 and taken along line 9-9 of FIG. 8.

The internal area 132 of the dispenser assembly 100 of the second preferred embodiment includes a first gear 152 and a second gear 162. It is to be understood that this configuration could be varied and the gear drive could be configured differently without deviating from the scope of this invention. As shown in FIG. 9, it will be seen that a third pin 144 is used as the feeder for the bandage carrier 11 where a pre-wound roll 141 of the bandage carrier 11 is rotatably and removably pre-wrapped about the pin 144. Thus, when the second gear 162 is rotated in the clockwise direction as viewed in FIG. 9 by the motor 170, the bandage carrier 11 is pulled and the bandage carrier 11 unwinds itself from the pin 144. The second gear 162 has a plurality of teeth 166 defined about its perimeter. As shown in this particular embodiment, the teeth 166 of the second gear 162 mesh with gear teeth 156 of the first gear 152, the first gear 152 also including a centrally-disposed pin 154. Though not shown in this second embodiment, a first gear (not shown) could be used with the pin 144 and which would mesh with the gear teeth 156, 166 of the first and second gears 152, 162, respectively. The first gear 152 includes a pin 154 that is used to gather the remnant material of the first protective covering 50 that overlays the bandage carrier 11. Similarly, the second gear 162 is provided to gather the second protective layer 60 that overlays the bandage carrier 11. In application, as a user pushes the button 133, the bandage carrier 11 is fed from the assembly 100 by actuation of the motor 170 which rotates the second gear 162 in a clockwise direction. This, in turn, moves the first gear 152 in a counterclockwise direction. In this way, bandage carrier 11 is drawn from the pin 144 and waste covering material 50, 60 is taken up by the first gear 152 and pin 154 and the second gear 162 and pin 164, respectively.

Figure 10:
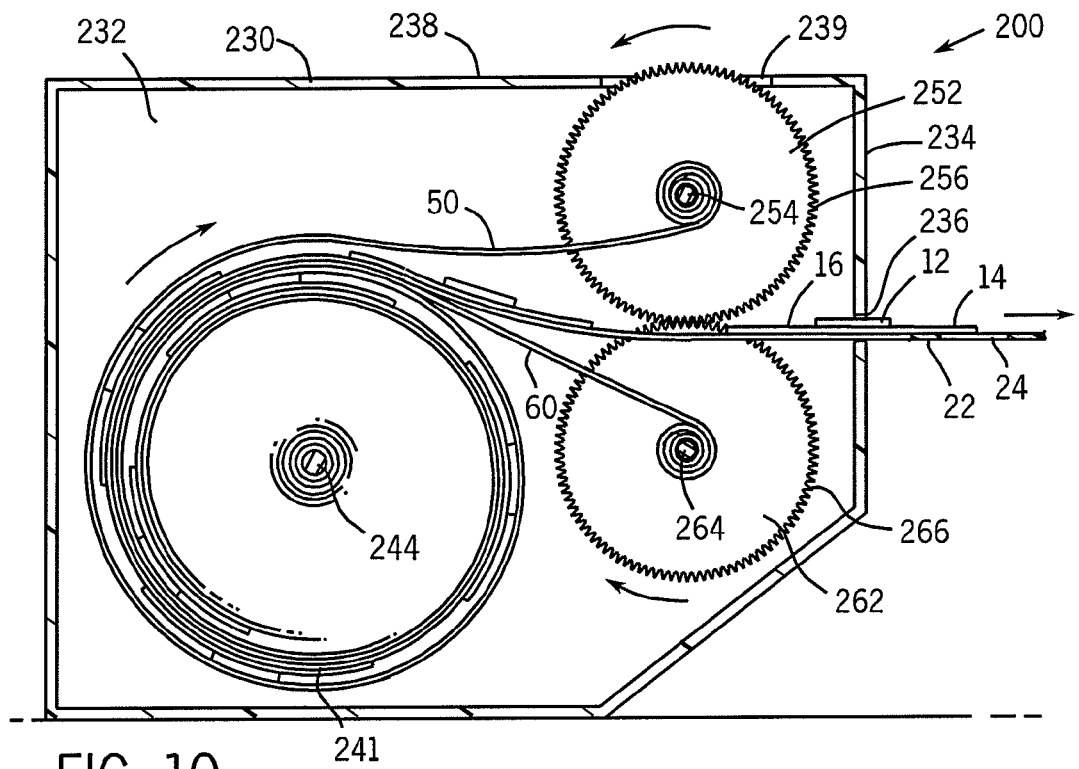
FIG. 10 is a top, front and left side perspective view of a third embodiment of an assembly that is used to dispense adhesive bandages from a carrier in accordance with the present invention.

FIG. 10 illustrates still another preferred embodiment of a dispenser assembly, generally identified 200, that is used to dispense bandage carrier 11 in accordance with the present invention. In general, this third embodiment of the dispenser assembly 200 includes a dispenser enclosure 230 that defines an interior area 232. The dispenser enclosure 230 includes a face 234 having an aperture 236 defined in it. As shown, the aperture 236 that is defined within the face 234 of the container 230 is a generally elongated and rectangular opening, as was the case with the prior embodiments and for the same reason. The aperture 236 must be able to allow the bandage carrier 11 to pass through it. The internal area 232 of the dispenser assembly 200 includes, in this third embodiment, a first gear 252 having a centrally-disposed pin 254 and a second gear 262 also having a centrally-disposed pin 264. The first gear 252 also has a plurality of gear teeth 256 defined about its perimeter and the second gear 262 has a plurality of gear teeth 266 defined about its perimeter as well. As shown in FIG. 10, the container 230 includes a second face 238 having a generally slotted aperture 239 defined in it. The purpose of the slotted aperture 239 is to allow a portion of the first gear 252 to extend through the aperture 239. In this way, the user may use his or her thumb to engage the gear teeth 256 of the first gear 252 and manually rotate that first gear 252 about its centrally-disposed pin 254. It is to be understood that this "thumb-wheel" configuration could be varied and the gear drive could be placed or located differently without deviating from the scope of this invention. As shown in FIG. 10, it will be seen that a third pin 244 is used as a feeder for the bandage carrier 11 where a pre-wound roll 241 of the bandage carrier 11 is secured about the pin 244. Thus, when the first gear 252 is rotated in the counterclockwise direction as viewed in FIG. 10 by the user's thumb (not shown), the bandage carrier 11 is pulled and becomes unwound from the pin 144. The second gear 262 has a plurality of teeth 266 defined about its perimeter as well. As shown in this particular embodiment, the teeth 266 of the second gear 262 mesh with gear teeth 256 of the first gear 252. Though not shown in this third embodiment, a first gear (not shown) could be used with the pin 144 and which would mesh with the gear teeth 256, 266 of the first and second gears 252, 262, respectively. The centrally-disposed pin 254 of the first gear 252 is used to gather the remnant material of the first protective covering 50 that overlays the bandage carrier 11. Similarly, the second gear 262 is provided to gather the second protective layer 60 that overlays the bandage carrier 11 about the pin 264 of that gear 262.

Figure 11:
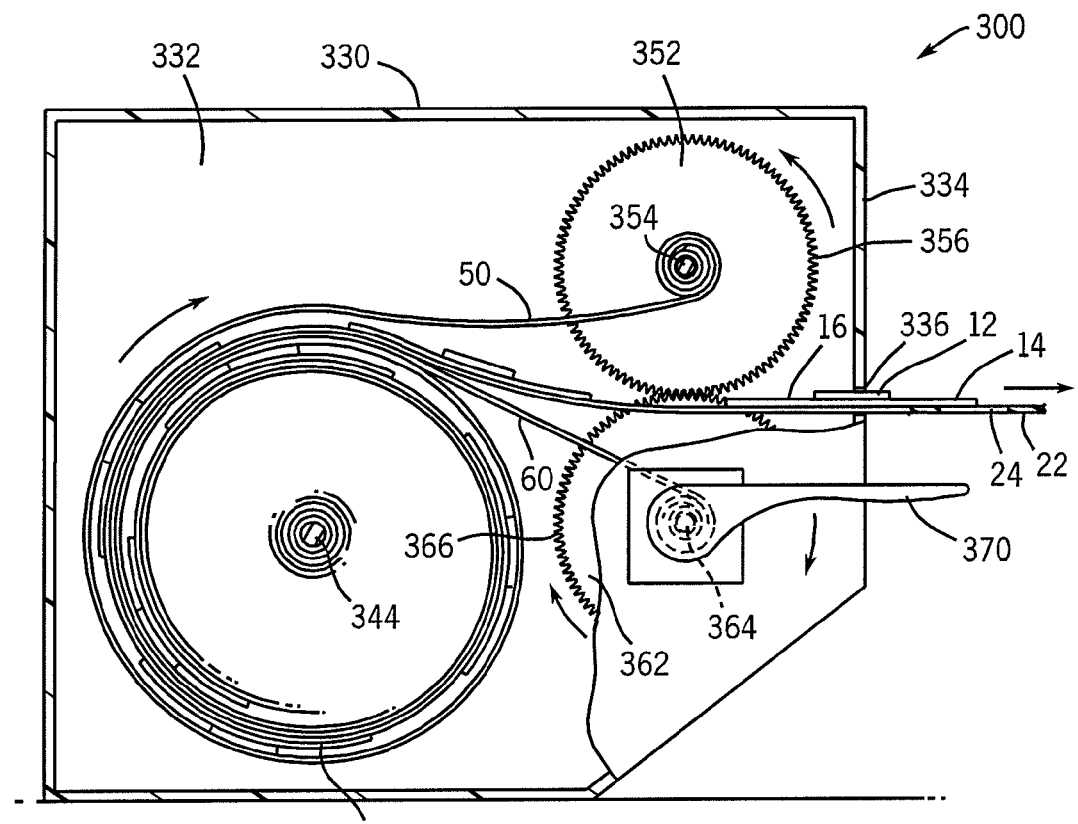
FIG. 11 is a top, front and left side perspective view of a fourth embodiment of an assembly that is used to dispense adhesive bandages from a carrier in accordance with the present invention.

Referring now to FIG. 11, it illustrates a fourth preferred embodiment of a dispenser assembly generally identified 300, that is used to dispense bandage carrier in accordance with the present invention. In general, the dispenser assembly 300 includes a dispenser enclosure 330 that defines an interior area 332. The dispenser enclosure 330 includes a face 334 having an aperture 336 defined in it. As shown, the opening 336 that is defined within the face 334 of the container 330 is a generally elongated and rectangular opening. Again, the reason for that configuration is that the opening 336 must be able to allow the bandage carrier 11 to freely pass through it. The internal area 332 of the dispenser assembly 300 includes, in the fourth embodiment, a first gear 352 and a second gear 362. It is to be understood that this configuration could be varied and the gear drive could be configured differently without deviating from the scope of this invention. As shown in FIG. 11, it will be seen that a third pin 344 is also used as a feeder for the bandage carrier 11 where a pre-wound roll 341 of the bandage carrier 11 is wrapped around the pin 344. When the second gear 362 is rotated in the clockwise direction as viewed in FIG. 11, the bandage carrier 11 is pulled and becomes unwound from the pin 344. The second gear 362 is actuated by means of a push lever 370. In this preferred embodiment, the push lever 370 is rotatably movable a short distance and is spring-loaded to return the push lever 370 to its original position following actuation by the user. The second gear 362 has a plurality of teeth 366 defined about its perimeter. As shown in this particular embodiment, the teeth 366 of the second gear 362 mesh with gear teeth 356 of the first gear 352, the first gear 352 also including a centrally-disposed pin 354. Though not shown in this fourth "push lever" embodiment, a first gear (not shown) could be used with the pin 344 and which would mesh with the gear teeth 356, 366 of the first and second gears 352, 362, respectively. The pin 354 of the first gear 352 is used to gather the remnant material of the first protective covering 50 that overlays the bandage carrier 11. Similarly, the second gear 362 is provided to gather the second protective layer 60 that overlays the bandage carrier 11. In application, the bandage carrier 11 is fed from the assembly 300 as a user pushes the lever 370 downwardly which rotates the second gear 362 in a clockwise direction. The push lever 370 may be spring-loaded (not shown) to return the push lever 370 to its original position. A ratchet-and-pawl subassembly (also not shown) may be used to allow pushing of the lever 370 in one direction only. Pushing the lever 370, in turn, moves the first gear 352 in a counterclockwise direction. In this way, bandage carrier 11 is drawn from the pin 344 and waste covering material 50, 60 is taken up by the first gear 352 and pin 354 and the second gear 362 and pin 364, respectively.

The principles of this invention having been fully explained in connection with the foregoing, I hereby claim as my invention:

1. An adhesive bandage carrier that comprises
   a longitudinally-extending carrier strip,
   a plurality of apertures defined within the carrier strip, said apertures being disposed along the carrier strip at substantially equal intervals, and a plurality of bandages, each bandage including a first edge and said bandages being removably secured to the carrier strip such that the bandage first edge overlays one of the plurality of carrier strip apertures defined within the carrier strip.

2. The adhesive bandage carrier of claim 1 wherein the plurality of bandages are longitudinally-disposed along the carrier strip at substantially equal intervals.

3. The adhesive bandage carrier of claim 1 wherein the plurality of bandages and the carrier strip are enveloped by a protective covering.

4. The adhesive bandage carrier of claim 3 wherein carrier strip comprises a top portion upon which the plurality of bandages are removably attached and a bottom portion and wherein the protective covering comprises a first protective covering element that overlays the top portion of the carrier strip and bandages and a second protective covering element that overlays the bottom portion of the carrier strip.

5. The adhesive bandage carrier of claim 4 wherein the first protective covering element and the second protective covering element are comprised of longitudinally-extending members having longitudinal edges that are sealed.

6. The adhesive bandage carrier of claim 4 wherein the first protective covering element and the second protective covering element are comprised of longitudinally-extending members having longitudinal edges that are releasably sealed to encapsulate the carrier when sealed along the longitudinal edges.

7. An assembly for dispensing an adhesive bandage carrier, said adhesive bandage carrier comprising a longitudinally-extending carrier strip, a plurality of apertures defined within the carrier strip, said apertures being disposed along the carrier strip at substantially equal intervals, and a plurality of bandages, each bandage including a first edge and said bandages being removably secured to the carrier strip such that a portion of the bandage first edge overlays a carrier strip aperture, the assembly comprising
a dispenser container, and
a feed means for delivering carrier strip from within the container to the outside of the container.

8. The dispensing assembly of claim 7 wherein the plurality of bandages are longitudinally-disposed along the carrier strip at substantially equal intervals and the plurality of bandages and the carrier strip are enveloped by a protective covering, said protective covering comprising a first protective covering element that overlays the top portion of the carrier strip and bandages and a second protective covering element that overlays the bottom portion of the carrier strip.

9. The dispensing assembly of claim 8 wherein the first protective covering element and the second protective covering element are comprised of longitudinally-extending members having longitudinal edges that are sealed and the assembly further comprises means for removing and taking up the first and second protective covering elements as they are removed from the bandage carrier.

10. The dispensing assembly of claim 9 wherein the bandage feed means comprises a first pin about which a continuous roll of carrier strip may be wrapped.

11. The dispensing assembly of claim 10 wherein the removing and taking-up means comprises a second pin about which the first protective covering element may be wrapped and a third pin about which the second protective covering element may be wrapped.

12. The dispensing assembly of claim 11 wherein the feed means further comprises a first gear that is attached to the first pin, and the removing and taking-up means comprises a second gear that is attached to the second pin, and a third gear that is attached to the third pin.

13. The dispensing assembly of claim 12 wherein the first, second and third gears are toothed and the teeth of the gears are meshed to cooperatively rotate when carrier is pulled manually from the assembly.

14. The dispensing assembly of claim 11 wherein the removing and taking-up means comprises a first gear that is attached to the second pin, and a second gear that is attached to the third pin, the first and second gears being toothed and the teeth of the gears being meshed to cooperatively rotate when one of the gears is manually rotated.

15. The dispensing assembly of claim 14 further comprising a push lever for manual rotation of one of the gears.

16. The dispensing assembly of claim 11 further comprising an electrical motor and wherein the removing and taking-up means comprises a first gear that is attached to the second pin, and a second gear that is attached to the third pin, the first and second gears being toothed and the teeth of the gears being meshed to cooperatively rotate when one of the gears is rotated by electrical actuation of the motor.

17. The dispensing assembly of claim 16 further comprising a push button or an infrared sensor for electrical actuation of the motor.

18. An assembly for dispensing an adhesive bandage carrier, said adhesive bandage carrier comprising a longitudinally-extending carrier strip, a plurality of apertures defined within the carrier strip, said apertures being disposed along the carrier strip at substantially equal intervals, and a plurality of bandages, each bandage including a first edge and said bandages being removably secured to the carrier strip such that a portion of the bandage first edge overlays a carrier strip aperture, wherein the plurality of bandages are longitudinally-disposed along the carrier strip at substantially equal intervals and the plurality of bandages and the carrier strip are enveloped by a protective covering, said protective covering comprising a first protective covering element that overlays the top portion of the carrier strip and bandages and a second protective covering element that overlays the bottom portion of the carrier strip, wherein the first protective covering element and the second protective covering element are comprised of longitudinally-extending members having longitudinal edges that are sealed, the assembly comprising
a dispenser container,
a feed means for delivering carrier strip from within the container to the outside of the container, and
means for removing and taking up the first and second protective covering elements as they are removed from the bandage carrier.

19. The dispensing assembly of claim 18 wherein said feed means comprises a first rotational means, and said removing and taking up the protective covering elements comprises a second rotational means and a third rotational means.

20. The dispensing assembly of claim 18 wherein the first rotational means comprises a first pin about which a continuous roll of carrier strip may be wrapped and wherein the second rotational means comprises a second pin about which the first protective covering element may be wrapped and a third rotational means comprises a third pin about which the second protective covering element may be wrapped.

21. The dispensing assembly of claim 20 wherein the first rotational means further comprises a first gear that is attached to the first pin, and the second rotational means comprises a second gear that is attached to the second pin, and the third rotational means comprises a third gear that is attached to the third pin.

22. The dispensing assembly of claim 21 wherein the first, second and third gears are toothed and the teeth of the gears are meshed to cooperatively rotate when carrier is pulled manually from the assembly.

23. The dispensing assembly of claim 20 wherein the removing and taking-up means comprises a first gear that is attached to the second pin, and a second gear that is attached to the third pin, the first and second gears being toothed and the teeth of the gears being meshed to cooperatively rotate when one of the gears is manually rotated.

24. The dispensing assembly of claim 23 further comprising a push lever for manual rotation of one of the gears.

25. The dispensing assembly of claim 20 further comprising an electrical motor and wherein the removing and taking-up means comprises a first gear that is attached to the second pin, and a second gear that is attached to the third pin, the first and second gears being toothed and the teeth of the gears being meshed to cooperatively rotate when one of the gears is rotated by electrical actuation of the motor.

26. The dispensing assembly of claim 25 further comprising a push button or infrared for electrical actuation of the motor.

* * * * *